US011642087B2

(12) United States Patent
Abdul Majeed et al.

(10) Patent No.: US 11,642,087 B2
(45) Date of Patent: May 9, 2023

(54) METHOD AND APPARATUS FOR PRE-PROCESSING PPG SIGNAL

(71) Applicant: SAMSUNG ELECTRONICS CO., LTD., Suwon-si (KR)

(72) Inventors: Ibrahim Abdul Majeed, Calicut (IN); Sujit Jos, Bangalore (IN); Rahul Arora, Kanput (IN); Ka Ram Choi, Hwaseong-si (KR); Sang Kon Bae, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 746 days.

(21) Appl. No.: 16/749,514

(22) Filed: Jan. 22, 2020

(65) Prior Publication Data
US 2020/0237312 A1  Jul. 30, 2020

(30) Foreign Application Priority Data

Jan. 25, 2019 (IN) .............................. 201941003111
Nov. 29, 2019 (KR) ......................... 10-2019-0156303

(51) Int. Cl.
*A61B 5/00* (2006.01)
*A61B 5/024* (2006.01)

(52) U.S. Cl.
CPC ........ *A61B 5/7214* (2013.01); *A61B 5/02416* (2013.01); *A61B 5/725* (2013.01); *A61B 5/7278* (2013.01)

(58) Field of Classification Search
CPC ... A61B 5/02416; A61B 5/7214; A61B 5/725; A61B 5/7278
See application file for complete search history.

(56) References Cited

U.S. PATENT DOCUMENTS

| 7,613,486 | B2 | 11/2009 | Yeo et al. |
| 8,050,730 | B2 | 11/2011 | Zhang et al. |
| 8,784,322 | B2 | 7/2014 | Kim et al. |
| 9,380,954 | B2 | 7/2016 | Lee et al. |
| 9,855,012 | B2 | 1/2018 | Banerjee et al. |
| 2004/0220483 | A1 | 11/2004 | Yeo et al. |

(Continued)

FOREIGN PATENT DOCUMENTS

KR    10-2004-0067240 A    7/2004
KR       10-0809041 A       3/2008

OTHER PUBLICATIONS

Chungkeun Lee et al., "Relations between ac-dc components and optical path length in photoplethysmography", Journal of Biomedical Optics 16 (7), 077012, Jul. 2011 (5 pages total).

(Continued)

*Primary Examiner* — Mark D Remaly
(74) *Attorney, Agent, or Firm* — Sughrue Mion, PLLC

(57) ABSTRACT

A method and apparatus for pre-processing a photoplethysmogram (PPG) signal include receiving, by an apparatus, the PPG signal including a plurality of pulses, obtaining, by the apparatus, a smoothed PPG signal based on smoothing the PPG signal using a moving average filter, obtaining, by the apparatus, a drift removed PPG signal based on removing drift from the smoothed PPG signal using a fitted polynomial function, and obtaining, by the apparatus, a rectified PPG signal based on correcting a motion artifact of the drift removed PPG signal by replacing each of the plurality of pulses using a combination of a global signal pulse and a corresponding local signal pulse.

20 Claims, 13 Drawing Sheets

(56) References Cited

U.S. PATENT DOCUMENTS

| | | |
|---|---|---|
| 2008/0009685 A1 | 1/2008 | Kim et al. |
| 2015/0148691 A1 | 5/2015 | Moyer et al. |
| 2017/0164842 A1 | 6/2017 | Koppel et al. |
| 2018/0199849 A1 | 7/2018 | Axelrod et al. |

OTHER PUBLICATIONS

Rohan Jaishankar, "A Spectral Approach for Noninvasive Estimation of Intracranial Pressure", Massachusetts Institute of Technology, Jun. 2017, pp. 1-101, (101 pages total).

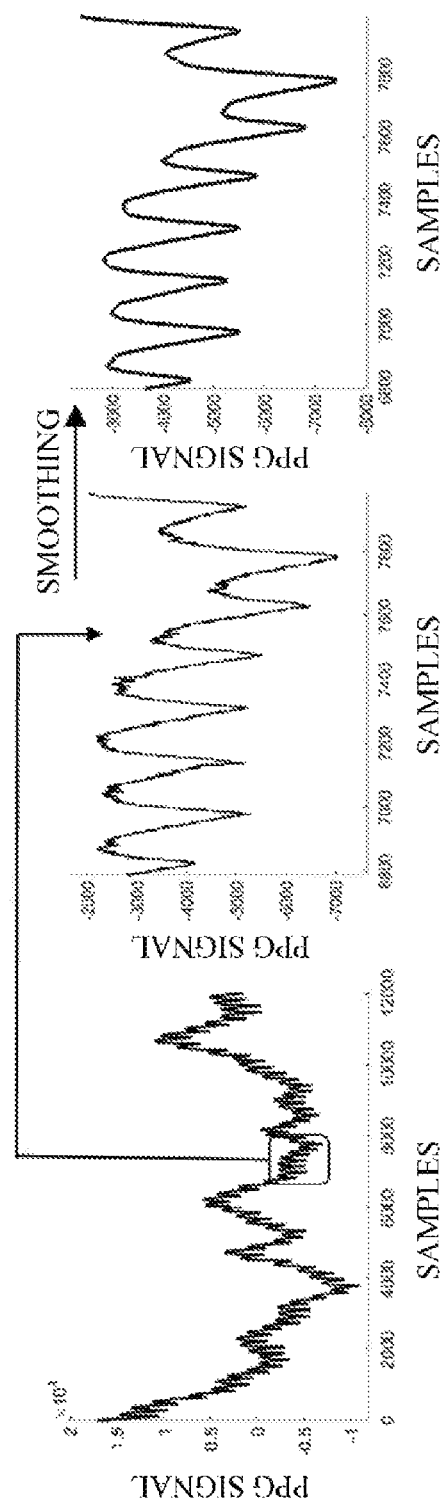

METHOD AND APPARATUS FOR PRE-PROCESSING PPG SIGNAL

CROSS-REFERENCE TO RELATED APPLICATION(S)

This applications claims priority from Korean Patent Application No. 10-2019-0156303, filed on Nov. 29, 2019, in the Korean Intellectual Property Office, and Indian Patent Application No. 201941003111, filed on Jan. 25, 2019, in the Indian Patent Office, the disclosures of which are incorporated herein by reference in their entireties.

BACKGROUND

1. Field

Apparatuses and methods consistent with example embodiments relate to signal processing, and more specifically relates to pre-processing a photoplethysmogram (PPG) signal.

2. Description of Related Art

PPG signals are used for measuring human vital signs such as blood pressure, blood oxygen (e.g., SpO2), heart rate, etc. PPG signals are generally affected by various noise, drift, and motion artifacts. Motion artifacts may have the greatest impact on the quality of PPG signals because motion artifacts affect the individual pulses, and therefore affect features that are based mostly on the morphology of the pulses. Removing the motion artifacts without influencing the PPG signals is an important task in PPG signal pre-processing. Frequency-based and time-frequency-based methods exist for motion artifact removal. However, such techniques are prone to simultaneously removing portions of the PPG signal because the frequency bands of motion artifacts and the PPG signal overlap. Thus, removing motion artifacts using frequency domain methods may also remove signal content of the PPG signals.

SUMMARY

According to an aspect of an example embodiment, there is provided a method for pre-processing a photoplethysmogram (PPG) signal including receiving, by an apparatus, the PPG signal including a plurality of pulses, obtaining, by the apparatus, a smoothed PPG signal based on smoothing the PPG signal using a moving average filter, obtaining, by the apparatus, a drift removed PPG signal based on removing drift from the smoothed PPG signal using a fitted polynomial function, and obtaining, by the apparatus, a rectified PPG signal based on correcting a motion artifact of the drift removed PPG signal by replacing each of the plurality of pulses using a combination of a global signal pulse and a corresponding local signal pulse.

The method may include extracting, by the apparatus, a feature from the rectified PPG signal, and predicting, by the apparatus, a vital signal based on the extracted feature.

Obtaining the drift removed PPG signal may include determining the fitted polynomial function as a polynomial approximation of a predefined degree of the smoothed PPG signal, and subtracting the fitted polynomial function from the smoothed PPG signal to obtain the drift removed PPG signal.

The method may include dividing each pulse of the drift removed PPG signal into an ascending pulse and a descending pulse based on troughs and peaks of the drift removed PPG signal, obtaining an average ascending length as an average of a number of samples in each ascending pulse, obtaining an average descending length as an average of a number of samples in each descending pulse, resampling each ascending pulse to the average ascending length using linear interpolation to obtain a plurality of resampled ascending pulses, resampling each descending pulse to the average descending length using linear interpolation to obtain a plurality of resampled descending pulses, obtaining an average ascending pulse as an average of the plurality of resampled ascending pulses, obtaining an average descending pulse as an average of the plurality of resampled descending pulses, and determining the global signal pulse by concatenating the average ascending pulse and the average descending pulse.

The method may include isolating a predefined number of local pulses of the drift removed PPG signal around the local pulse to be rectified, dividing each of the local signal pulses into a local ascending pulse and a local descending pulse, resampling each local ascending pulse to an average ascending length using linear interpolation to obtain a plurality of resampled local ascending pulses, resampling each local descending pulse to an average descending length using linear interpolation to obtain a plurality of resampled local descending pulses, obtaining an average local ascending pulse as the average of the plurality of resampled local ascending pulses, obtaining an average local descending pulse as the average of the plurality of resampled local descending pulses, and determining the local signal pulse by concatenating the average local ascending pulse and the average local descending pulse.

Obtaining the rectified PPG signal may include obtaining an intermediate rectified PPG signal by replacing each local signal pulse using a convex combination of the corresponding local signal pulse and the global signal pulse, and resampling each pulse in the intermediate rectified PPG signal to a number of samples in the corresponding pulse of the drift removed PPG signal.

Resampling each pulse in the intermediate rectified PPG signal to the number of samples in the corresponding pulse of the drift removed PPG signal may include dividing each pulse in the intermediate rectified PPG signal into an ascending pulse and a descending pulse, wherein a number of samples in the ascending pulse is the average ascending length and number of samples in the descending pulse is the average descending length, resampling each ascending pulse to the number of samples in the ascending pulse of the corresponding pulse in the drift removed PPG signal to obtain a rectified ascending pulse, resampling each descending pulse to the number of samples in the descending pulse of the corresponding pulse in the drift removed PPG signal to obtain a rectified descending pulse, and concatenating each rectified ascending pulse with the corresponding rectified descending pulse to obtain the rectified PPG signal.

The troughs and the peaks may denote sample indices corresponding to troughs and peaks in the smoothed PPG signal.

The method may include removing peaks that occur before a first trough or after a last trough.

The feature may include at least one of a mean of a Kaizer Teager Energy (KTE) feature, a variance of the KTE feature, a skewness of the KTE feature, a Spectral Entropy feature, and a Spectral Energy Logarithmic feature.

According to an aspect of another example embodiment, there is provided an apparatus for pre-processing a photoplethysmogram (PPG) signal that includes a processor configured to receive the PPG signal including a plurality of pulses, obtain a smoothed PPG signal based on smoothing the PPG signal, obtain a drift removed PPG signal based on removing drift from the smoothed PPG signal using a fitted polynomial function, and obtain a rectified PPG signal based on correcting a motion artifact of the drift removed PPG signal by replacing each of the plurality of pulses using a combination of a global signal pulse and a corresponding local signal pulse.

The processor may extract a feature from the rectified PPG signal, and predict a vital signal based on the extracted feature.

The processor may determine the fitted polynomial function as a polynomial approximation of a predefined degree of the smoothed PPG signal, and subtract the fitted polynomial function from the smoothed PPG signal to obtain the drift removed PPG signal.

The processor may divide each pulse of the drift removed PPG signal into an ascending pulse and a descending pulse based on troughs and peaks of the drift removed PPG signal, obtain an average ascending length as an average of a number of samples in each ascending pulse, obtain an average descending length as an average of a number of samples in each descending pulse, resample each ascending pulse to the average ascending length using linear interpolation to obtain a plurality of resampled ascending pulses, resample each descending pulse to the average descending length using linear interpolation to obtain a plurality of resampled descending pulses, obtain an average ascending pulse as the average of the plurality of resampled ascending pulses, obtain an average descending pulse as the average of the plurality of resampled descending pulses, and determine the global signal pulse by concatenating the average ascending pulse and the average descending pulse.

The processor may isolate a predefined number of local pulses around the pulse to be rectified, divide each of the local pulses into a local ascending pulse and a local descending pulse, resample each local ascending pulse to the average ascending length using linear interpolation to obtain a plurality of resampled local ascending pulses, resample each local descending pulse to the average descending length using linear interpolation to obtain a plurality of resampled local descending pulses, obtain an average local ascending pulse as the average of the plurality of resampled local ascending pulses, obtain an average local descending pulse as the average of the plurality of resampled local descending pulses, and determine the local signal pulse by concatenating the average local ascending pulse and the average local descending pulse.

The processor may obtain an intermediate rectified PPG signal by replacing each local signal pulse using a convex combination of the corresponding local signal pulse and the global signal pulse, and resample each pulse in the intermediate rectified PPG signal to a number of samples in the corresponding pulse of the drift removed PPG signal.

The processor may divide each pulse in the intermediate rectified PPG signal into an ascending and a descending pulse, wherein a number of samples in the ascending pulse is the average ascending length and a number of samples in the descending pulse is the average descending length, resample each ascending pulse to the number of samples in the ascending pulse of the corresponding pulse in the drift removed PPG signal to obtain a rectified ascending pulse, and resample each descending pulse to the number of samples in the descending pulse of the corresponding pulse in the drift removed PPG signal to obtain a rectified descending pulse; and concatenate each rectified ascending pulse with the corresponding rectified descending pulse to obtain the rectified PPG signal.

The troughs and the peaks may denote sample indices corresponding to troughs and peaks in the smoothed PPG signal.

The processor may remove peaks that occur before a first trough or after a last trough.

The feature may include at least one of a mean of a Kaizer Teager Energy (KTE) feature, a variance of the KTE feature, a skewness of the KTE feature, a Spectral Entropy feature, and a Spectral Energy Logarithmic feature.

BRIEF DESCRIPTION OF THE DRAWINGS

The above and/or other aspects of the present disclosure will be more apparent from the following description of example embodiments taken in conjunction with the accompanying drawings, in which:

FIGS. 8A through 8C are example diagrams in which the smoothed PPG signal is depicted after applying a moving average filter, according to an example embodiment;

DETAILED DESCRIPTION

Figure 1:
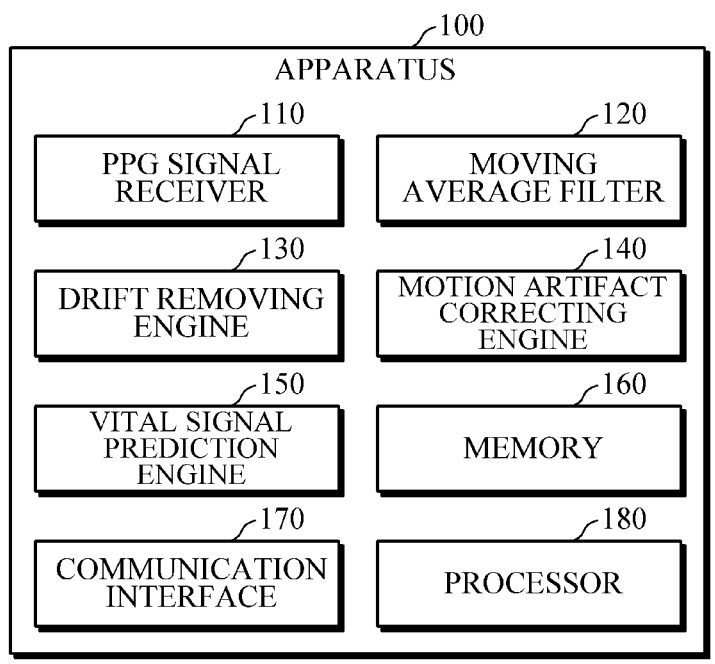
FIG. 1 is a block diagram of an apparatus for pre-processing a PPG signal, according to an example embodiment.

The example embodiments herein and the various features and details thereof are explained more fully with reference to the accompanying drawings. Descriptions of well-known components and processing techniques may be omitted so as to not unnecessarily obscure the embodiments herein. Also, the various embodiments described herein are not necessarily mutually exclusive, as some embodiments may be combined with one or more of other embodiments to form different embodiments. The term "or" as used herein, is non-exclusive, unless otherwise indicated. The examples used herein are intended to facilitate an understanding of ways in which the example embodiments herein may be practiced and to further enable those skilled in the art to practice the example embodiments herein. Accordingly, the examples should not be construed as limiting the scope of the example embodiments herein.

The example embodiments may be described and illustrated in terms of blocks which carry out a described function or functions. These blocks, which may be referred to herein as "units," "modules," or the like, and may be physically implemented by analog or digital circuits such as logic gates, integrated circuits, microprocessors, microcontrollers, memory circuits, passive electronic components, active electronic components, optical components, hardwired circuits, or the like, and may optionally be driven by firmware and software. The circuits may, for example, be embodied in one or more semiconductor chips, or on substrate supports such as printed circuit boards, and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the disclosure. The blocks of the example embodiments may be physically combined without departing from the scope of the disclosure.

The accompanying drawings are used to assist in understanding various technical features and it should be understood that the example embodiments presented herein are not limited by the accompanying drawings. As such, the present disclosure should be construed to extend to any modifications, equivalents and substitutes in addition to those which are particularly set out in the accompanying drawings. Terms such as "first," "second," etc. may be used herein to describe various elements, and these elements should not be limited by these terms. These terms are generally used to distinguish one element from another.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Accordingly, example embodiments herein provide a method for pre-processing a PPG signal. The method includes receiving, by an apparatus, the PPG signal including a plurality of pulses. Further, the method includes smoothing, by the apparatus, the PPG signal using a moving average filter to obtain a smoothed PPG signal. Further, the method includes removing, by the apparatus, drift from the smoothed PPG signal using a fitted polynomial function to obtain a drift removed PPG signal. Further, the method includes correcting, by the apparatus, a motion artifact of the drift removed PPG signal by replacing pulses using a combination of a global signal pulse and a local signal pulse to obtain a rectified PPG signal.

In contrast to conventional methods and systems, example embodiments described herein may correct the motion artifact of the drift removed PPG signal without requiring additional sensors and without significantly influencing a reference signal.

The example embodiments described herein may be used to calculate an average pulse by splitting each pulse into an ascending pulse and a descending pulse. In this way, example embodiments described herein may generate more accurate pulse averages and may provide improved motion artifact correction. The example embodiments described herein may be used to rectify each pulse using a convex combination of a local signal pulse and a global signal pulse. In this way, the embodiments described herein may reduce rectified signal degradation in the event that motion artifacts exist for longer periods.

The example embodiments described herein may be used to resample the rectified pulses to permit the period information, which might be lost during the calculation of the averages, to be preserved. The time series-based pre-processing example embodiments described herein may be used to remove noise effects, with emphasis on motion artifact correction.

The example embodiments described herein may consider a local signal pulse along with a global signal pulse. Further, the example embodiments described herein may be used to separately estimate an average ascending and a descending pulse. Further, intermediate rectified pulses may be resampled to the original number of samples to prevent the pulse period information from being lost. In this way, example embodiments described herein may provide more accurate pre-processing of the PPG signal.

FIG. 1 is a block diagram of an apparatus 100 for pre-processing a PPG signal, according to an example embodiment. The apparatus 100 may be, for example, a cellular phone, a smart phone, a Personal Digital Assistant (PDA), a tablet computer, a laptop computer, a smart watch, a smart band, a smart ring, or the like. In an example embodiment, the apparatus 100 includes a PPG signal receiver 110, a moving average filter 120, a drift removing engine 130, a motion artifact correcting engine 140, a vital signal prediction engine 150, a memory 160, a communication interface 170, and a processor 180.

The PPG signal receiver 110 is configured to receive a PPG signal including a plurality of pulses. Based on receiving the PPG signal, a moving average filter 120 is configured to smooth the PPG signal to obtain a smoothed PPG signal. As an example, FIG. 8A depicts the PPG signal. Further, FIG. 8B depicts a portion of the PPG signal shown and bounded in FIG. 8A. Further still, FIG. 8C depicts the smoothed signal after applying the moving average filter 120.

The smoothing of the PPG signal may be performed using the moving average filter 120. In an example, a window size of 21 with equal weighting (e.g., all coefficients having a value of 1) is implemented for the moving average filter 120. The smoothing of the PPG signal may be performed using the smoothing function shown below:

$$S_{smooth}(i) = AVG\left(S\left(i - \frac{w}{2}\right):S\left(i + \frac{w}{2}\right)\right)$$

Based on the smoothed PPG signal, a drift removing engine 130 is configured to remove drift from the smoothed PPG signal using a fitted polynomial function to obtain a drift removed PPG signal.

In an example embodiment, the drift removing engine 130 is configured to determine the fitted polynomial function as a polynomial approximation of a predefined degree of the smoothed PPG signal, and subtract the fitted polynomial function from the smoothed PPG signal to obtain the drift removed PPG signal. The degree of the polynomial may be based on the amount of drift and the length of the PPG signal.

In an example, the drift removal of the PPG signal may be performed using a polynomial fit of degree=30 for the entire PPG signal. The fitted polynomial is then subtracted from the signal to remove the drift as shown by the equations below.

$$P = \mathrm{polyfit}(S_{smooth}, \text{degree})$$

$$S_{drift\text{-}removed} = S_{smooth} - \mathrm{polyval}(P, \text{samples of } S_{smooth})$$

As shown above, the polyfit function provides the polynomial of degree "degree" which minimizes squared error loss with respect to $S_{smooth}$. The returned value P is a vector of degree+1 real numbers corresponding to the coefficients of the variables of the polynomial for degrees 0 to degree. polyval evaluates the polynomial P at the individual sampling points corresponding to $S_{smooth}$.

Figure 9A:
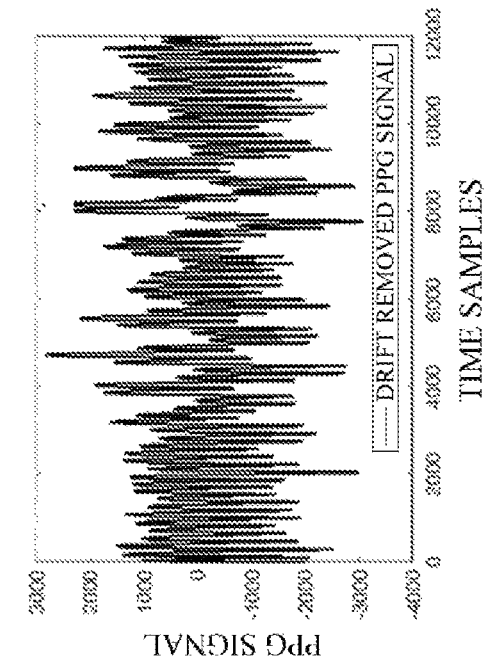
FIGS. 9A and 9B are example diagrams in which a drift removed signal is depicted, according to an example embodiment.
Figure 9B:
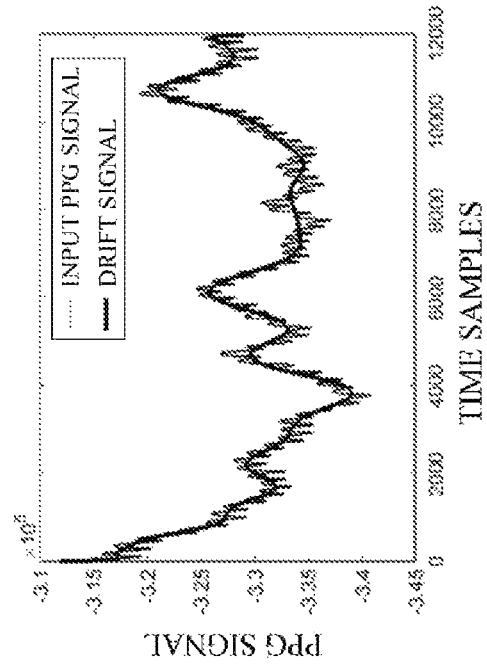

As shown in FIG. 9A, the dark grey line is the polynomial fit of the PPG signal. The drift removed signal is shown in FIG. 9B.

Based on the drift removed PPG signal, a motion artifact correcting engine 140 is configured to correct a motion artifact of the drift removed PPG signal by replacing pulses using a combination of a global signal pulse and corresponding local signal pulses to obtain a rectified PPG signal.

In an example embodiment, the motion artifact correcting engine 140 is configured to obtain an intermediate rectified PPG signal by replacing each local signal pulse using a convex combination of the local signal pulse and the global signal pulse. Further, the motion artifact correcting engine 140 is configured to divide each pulse in the intermediate rectified PPG signal into an ascending pulse and a descending pulse. A number of samples in the ascending pulse may be the average ascending length, and a number of samples in the descending pulse may be the average descending length. The average ascending length is obtained as the average of the number of samples in each ascending pulse, and the average descending length is obtained as the average of the number of samples in each descending pulse.

Further, the motion artifact correcting engine 140 is configured to resample each ascending pulse to the number of samples in the ascending pulse of the corresponding pulse in the drift removed PPG signal to obtain a rectified ascending pulse. Further, the motion artifact correcting engine 140 is configured to resample each descending pulse to the number of samples in the descending pulse of the corresponding pulse in the drift removed PPG signal to obtain a rectified descending pulse. Further, the motion artifact correcting engine 140 is configured to concatenate each rectified ascending pulse with the corresponding rectified descending pulse to obtain the rectified PPG signal.

In an example embodiment, the global signal pulse is determined by dividing each pulse of the drift removed PPG signal into an ascending pulse and a descending pulse based on troughs and peaks of the drift removed PPG signal, obtaining an average ascending length as the average of the number of samples in each ascending pulse, obtaining an average descending length as the average of the number of samples in each descending pulse, resampling each ascending pulse to the average ascending length using linear interpolation to obtain resampled ascending pulses, resampling each descending pulse to the average descending length using linear interpolation to obtain resampled descending pulses, obtaining an average ascending pulse as the average of all of the resampled ascending pulses, obtaining an average descending pulse as the average of all of the resampled descending pulses, and determining the global signal pulse by concatenating the average ascending pulse and the average descending pulse.

In an example embodiment, a trough and a peak denote sample indices corresponding to troughs and peaks in the smoothed PPG signal.

Sample index i is a trough if $S(i)=\min(S(i-K):S(i+K))$. K is one half of an expected minimum pulse width. In an example with a sample rate of 200 Hz, K was set to 35. Sample index i is a peak if $S(i)=\max(S(i-K):S(i+K))$.

Further, the motion artifact correcting engine 140 is configured to adjust the peaks and troughs by readjusting the troughs and peaks such that each trough is followed by a peak and vice versa. Further, peaks occurring before the first trough or after the last trough are removed. In this way, the signal starts and ends at a trough.

In an example embodiment, a local signal pulse is determined by isolating a predefined number of local pulses around the pulse to be rectified, dividing each of the local pulses into a local ascending pulse and a local descending pulse, resampling each local ascending pulse to the average ascending length using linear interpolation to obtain resampled local ascending pulses, resampling each local descending pulse to the average descending length using linear interpolation to obtain resampled local descending pulses, obtaining an average local ascending pulse as the average of all of the resampled local ascending pulses, obtaining an average local descending pulse as the average of all of the resampled local descending pulses, and determining the local signal pulse by concatenating the average local ascending pulse and the average local descending pulse.

In an example embodiment, the pulses to be replaced are determined by adjusting the peaks and the troughs such that peaks occurring before the first trough or after the last trough are removed such that complete pulses starting at a trough and ending at a trough are considered for rectification.

After obtaining the rectified PPG signal, the vital signal prediction engine 150 is configured to extract features from the rectified PPG signal, and predict a vital signal based on the extracted features. The vital signal may represent a blood pressure level, a blood oxygen level, a glucose value, a heart rate level, or the like. The feature may be, for example, a mean of a Kaizer Teager Energy (KTE) feature, a variance of the KTE feature, a skewness of the KTE feature, a Spectral Entropy feature, a Spectral Energy Logarithmic feature, or the like.

The processor 180 is configured to execute instructions stored in the memory 160 and to perform various processes. The communication interface 170 is configured to communicate internally between internal hardware components, and communicate externally with external devices via one or more networks. The processor 180 may include the moving average filter 120, the drift removing engine 130, the motion artifact correcting engine 140, and/or the vital signal prediction engine 150. That is, the processor 180 may be configured to perform some or all of the processes of the moving average filter 120, the drift removing engine 130, the motion artifact correcting engine 140, and/or the vital signal prediction engine 150.

The memory 160 stores instructions to be executed by the processor 180. The memory 160 may include non-volatile storage elements. Examples of such non-volatile storage elements may include magnetic hard discs, optical discs, floppy discs, flash memories, or forms of electrically programmable read-only memories (EPROMs) or electrically erasable and programmable read-only memories (EEPROMs). In addition, the memory 160 may, in some examples, be considered a non-transitory computer-readable storage medium. The term "non-transitory" may indicate that the storage medium is not embodied as a carrier wave or a propagating signal. In certain examples, a non-transitory storage medium may store data that may, over time, change (e.g., in Random Access Memory (RAM), or a cache).

Although FIG. 1 shows various components of the apparatus 100, it should be understood that other embodiments are not limited thereto. In other embodiments, the apparatus 100 may include a different number of components than as shown in FIG. 1, and/or different components than as shown in FIG. 1. Further, the labels or names of the components are used for illustrative purpose and should not limit the scope of the disclosure. Two or more components may be combined to perform a same or substantially similar function as another component(s) to process the PPG signal.

Figure 2:
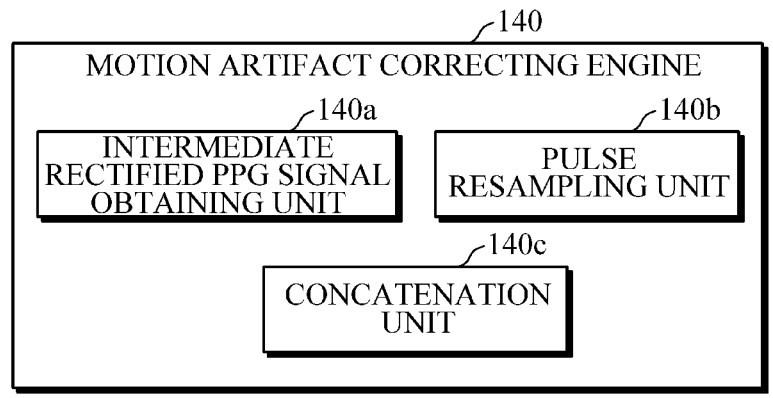
FIG. 2 is a block diagram of a motion artifact correcting engine included in the apparatus, according to an example embodiment.

FIG. 2 is a block diagram of the motion artifact correcting engine 140, according to an example embodiment. In an example embodiment, the motion artifact correcting engine 140 includes an intermediate rectified PPG signal obtaining unit 140a, a pulse resampling unit 140b, and a concatenation unit 140c.

The intermediate rectified PPG signal obtaining unit 140a is configured to obtain an intermediate rectified PPG signal by replacing each local signal pulse using a convex combination of the local signal pulse and the global signal pulse. Further, the intermediate rectified PPG signal obtaining unit 140a is configured to divide each pulse in the intermediate rectified PPG signal into an ascending pulse and a descending pulse. The number of samples in the ascending pulse is the average ascending length, and the number of samples in the descending pulse is the average descending length. The pulse resampling unit 140b is configured to resample each ascending pulse to the number of samples in the ascending pulse of the corresponding pulse in the drift removed PPG signal to obtain a rectified ascending pulse. The pulse resampling unit 140b is configured to resample each descending pulse to the number of samples in the descending pulse of the corresponding pulse in the drift removed PPG signal to obtain the rectified descending pulse. Further, the concatenation unit 140c is configured to concatenate the rectified ascending pulse with the corresponding rectified descending pulse to obtain the rectified PPG signal.

Although the FIG. 2 shows various components of the motion artifact correcting engine 140, it should be understood that other embodiments are not limited thereto. In other example embodiments, the motion artifact correcting engine 140 may include a different number of components than as shown in FIG. 2, and/or different components than as shown in FIG. 2. Further, the labels or names of the components are used for illustrative purpose and should not limit the scope of the disclosure. One or more components may be combined together to perform a same or substantially similar function as another component(s) to process the PPG signal.

Figure 3:
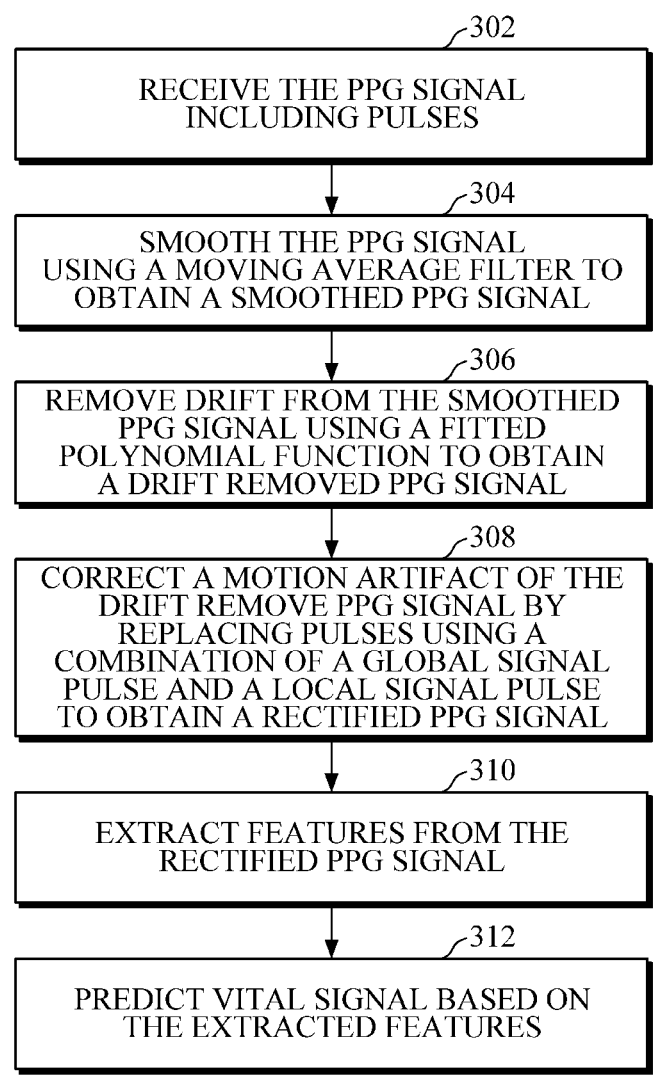
FIG. 3 is a flow diagram illustrating a method for pre-processing the PPG signal and extracting features for vital signal prediction, according to an example embodiment.

FIG. 3 is a flow diagram illustrating a method for preprocessing the PPG signal and extracting the features for vital signal prediction, according to an example embodiment. At operation 302, the method includes receiving the PPG signal including pulses. In an example embodiment, the PPG signal receiver 110 is configured to receive the PPG signal including a plurality of pulses.

At operation 304, the method includes smoothing the PPG signal using a moving average filter to obtain a smoothed PPG signal. In an example embodiment, the moving average filter 120 is configured to smooth the PPG signal to obtain the smoothed PPG signal.

At operation 306, the method includes removing drift from the smoothed PPG signal using a fitted polynomial function to obtain a drift removed PPG signal. In an example embodiment, the drift removing engine 130 is configured to remove drift from the smoothed PPG signal using the fitted polynomial function to obtain the drift removed PPG signal.

At operation 308, the method includes correcting a motion artifact of the drift removed PPG signal by replacing each pulse using a combination of a global signal pulse and a local signal pulse to obtain a rectified PPG signal. In an example embodiment, the motion artifact correcting engine 140 is configured to correct motion artifact of the drift removed PPG signal by replacing pulses using a combination of a global signal pulse and a local signal pulse to obtain a rectified PPG signal.

At operation 310, the method includes extracting features from the rectified PPG signal. In an example embodiment, the vital signal prediction engine 150 is configured to extract features from the rectified PPG signal.

At operation 312, the method includes predicting a vital signal based on the extracted features. In an example embodiment, the vital signal prediction engine 150 is configured to predict the vital signal based on the extracted features.

The various operations, actions, acts, blocks, steps, or the like, in the flow diagram may be performed in the presented order, in a different order, or simultaneously. Further, in some embodiments, some of the operations, actions, acts, blocks, steps, or the like, may be omitted, added, modified, skipped, or the like, without departing from the scope of the disclosure.

Figure 4:
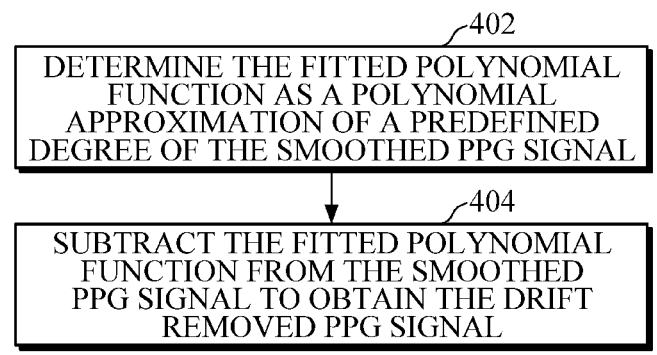
FIG. 4 is a flow diagram illustrating various operations for removing drift from a smoothed PPG signal using a fitted polynomial function to obtain a drift removed PPG signal, according to an example embodiment.

FIG. 4 is a flow diagram illustrating various operations for removing the drift from the smoothed PPG signal using the fitted polynomial function to obtain the drift removed PPG signal, according to an example embodiment. The operations (402 and 404) may be performed by the drift removing engine 130.

At operation 402, the method includes determining the fitted polynomial function as the polynomial approximation of a predefined degree of the smoothed PPG signal. At operation 404, the method includes subtracting the fitted polynomial function from the smoothed PPG signal to obtain the drift removed PPG signal.

The various operations, actions, acts, blocks, steps, or the like, in the flow diagram may be performed in the presented order, in a different order, or simultaneously. Further, in some embodiments, some of the operations, actions, acts, blocks, steps, or the like, may be omitted, added, modified, skipped, or the like without departing from the scope of the disclosure.

Figure 5:
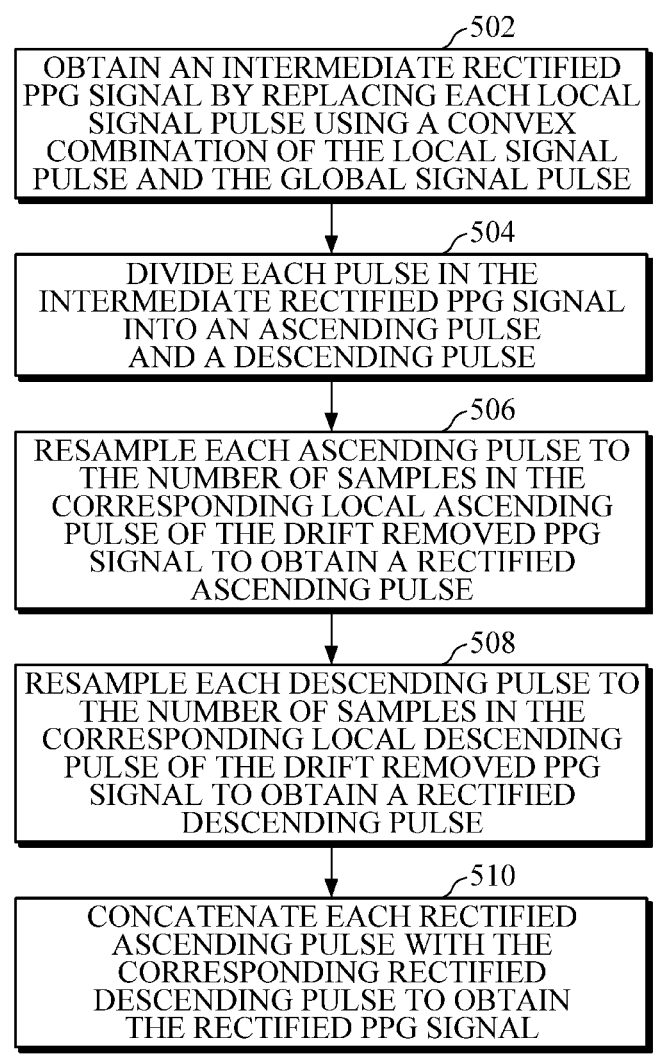
FIG. 5 is a flow diagram illustrating various operations for correcting a motion artifact of the drift removed PPG signal to obtain a rectified PPG signal, according to an example embodiment.

FIG. 5 is a flow diagram illustrating various operations for correcting the motion artifact of the drift removed PPG signal to obtain a rectified PPG signal, according to an example embodiment. The operations (502 to 510) may be performed by the motion artifact correcting engine 140.

At operation 502, the method includes obtaining an intermediate rectified PPG signal by replacing each local signal pulse using a convex combination of the local signal pulse and the global signal pulse. At operation 504, the method includes dividing each pulse in the intermediate rectified PPG signal into an ascending pulse and a descending pulse. The number of samples in the ascending pulse may be the average ascending length, and the number of samples in the descending pulse may be the average descending length. At operation 506, the method includes resampling each ascending pulse to the number of samples in the ascending pulse of the corresponding pulse in the drift removed PPG signal to obtain the rectified ascending pulse. At operation 508, the method includes resampling each descending pulse to the number of samples in the descending pulse of the corresponding pulse in the drift removed PPG signal to obtain the rectified descending pulse. At operation 510, the method includes concatenating each rectified ascending pulse with the corresponding rectified descending pulse to obtain the rectified PPG signal.

The various operations, actions, acts, blocks, steps, or the like, in the flow diagram may be performed in the presented order presented, in a different order, or simultaneously. Further, in some embodiments, some of the operations, actions, acts, blocks, steps, or the like, may be omitted, added, modified, skipped, or the like, without departing from the scope of the disclosure.

Figure 6:
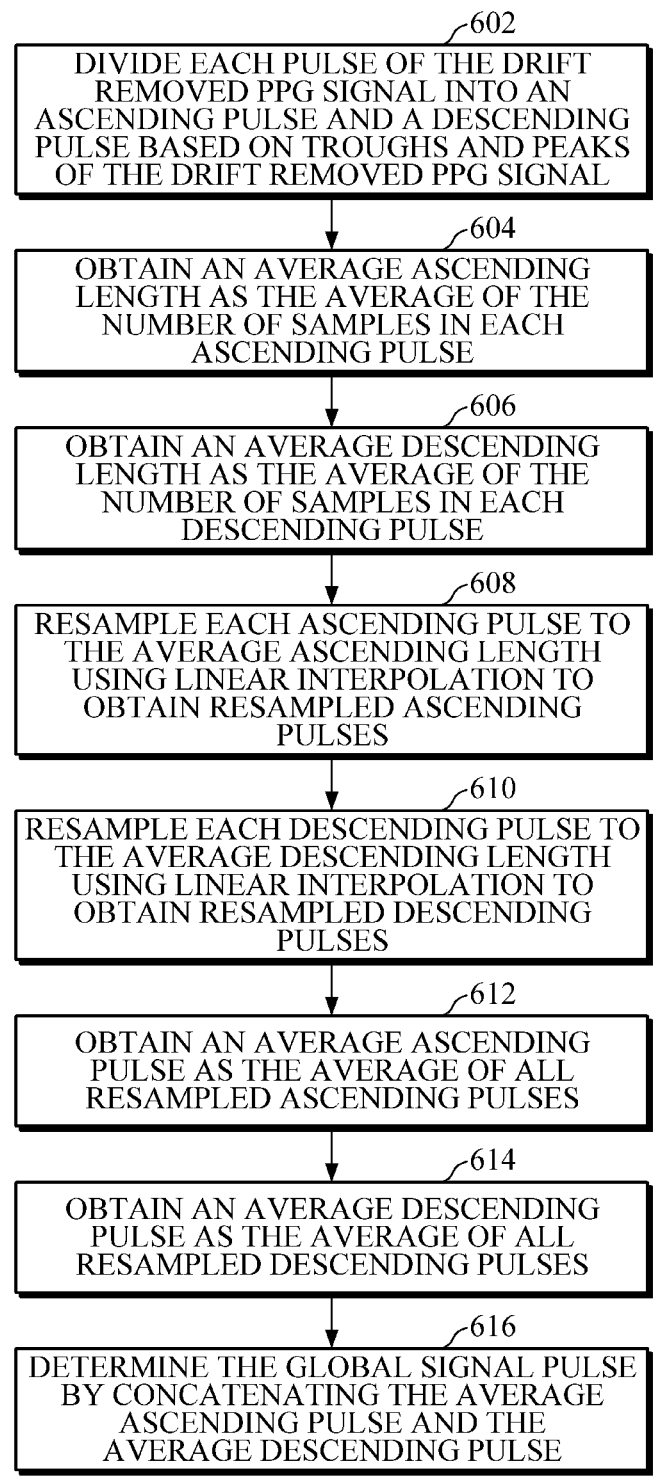
FIG. 6 is a flow diagram illustrating various operations for determining a global signal pulse, according to an example embodiment.

FIG. 6 is a flow diagram illustrating various operations for determining the global signal pulse, according to an example embodiment. The operations (602 to 616) may be performed by the motion artifact correcting engine 140.

At operation 602, the method includes dividing each pulse of the drift removed PPG signal into an ascending pulse and a descending pulse based on troughs and peaks of the drift removed PPG signal. At operation 604, the method includes obtaining an average ascending length as the average of the number of samples in each ascending pulse. At operation 606, the method includes obtaining an average descending length as the average of the number of samples in each descending pulse. At operation 608, the method includes resampling each ascending pulse to the average ascending length using linear interpolation to obtain resampled ascending pulses. At operation 610, the method includes resampling each descending pulse to the average descending length using linear interpolation to obtain resampled descending pulses. At operation 612, the method includes obtaining an average ascending pulse as the average of all resampled ascending pulses. At operation 614, the method includes obtaining the average descending pulse as the average of all resampled descending pulses. At operation 616, the method includes determining the global signal pulse by concatenating the average ascending pulse and the average descending pulse.

The various operations, actions, acts, blocks, steps, or the like, in the flow diagram may be performed in the presented order, in a different order, or simultaneously. Further, in some embodiments, some of the operations, actions, acts, blocks, steps, or the like may be omitted, added, modified, skipped, or the like without departing from the scope of the disclosure.

Figure 7:
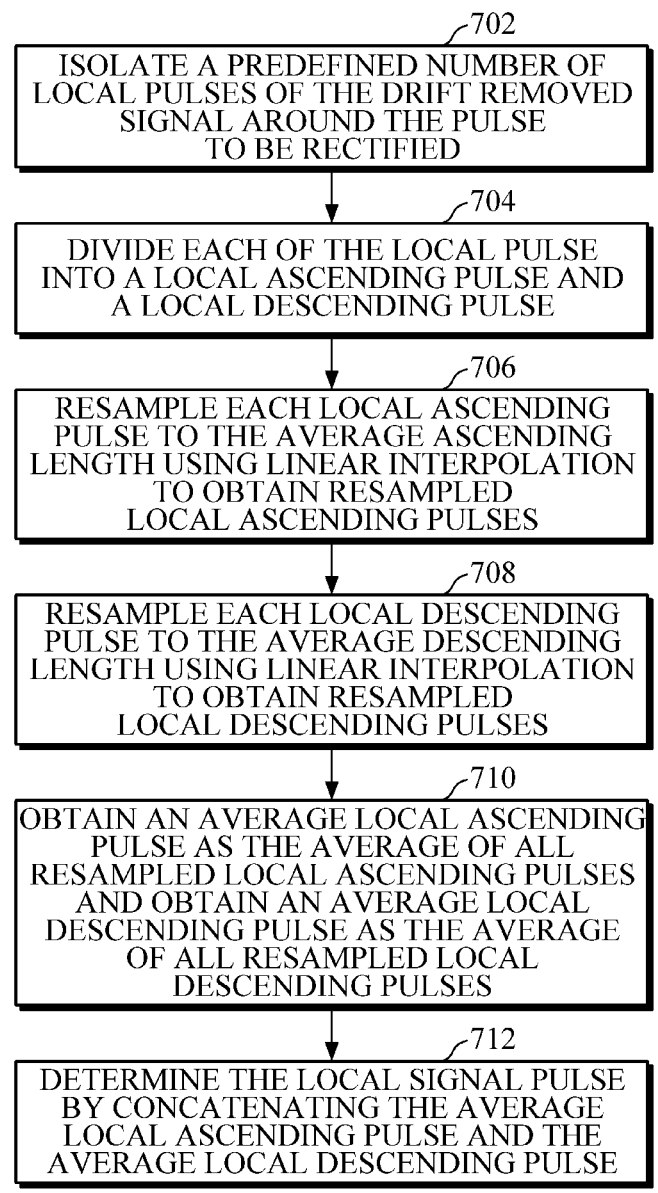
FIG. 7 is a flow diagram illustrating various operations for determining a local signal pulse, according to an example embodiment.

FIG. 7 is a flow diagram illustrating various operations for determining the local signal pulse, according to an example embodiment. The operations (702 to 712) may be performed by the motion artifact correcting engine 140.

At operation 702, the method includes isolating a predefined number of local pulses of the drift removed PPG signal around the pulse to be rectified. For example, a predefined number of pulses adjacent to the pulse to be rectified may be isolated. At operation 704, the method includes dividing each of the local pulses into a local ascending pulse and a local descending pulse. At operation 706, the method includes resampling each local ascending pulse to the average ascending length using linear interpolation to obtain resampled local ascending pulses. At operation 708, the method includes resampling each local descending pulse to the average descending length using linear interpolation to obtain resampled local descending pulses. At operation 710, the method includes obtaining the average local ascending pulse as the average of all resampled local ascending pulses, and obtaining the average local descending pulse as the average of all resampled local descending pulses. At operation 712, the method includes determining the local signal pulse by concatenating the average local ascending pulse and the average local descending pulse.

The various operations, actions, acts, blocks, steps, or the like, in the flow diagram may be performed in the presented order, in a different order, or simultaneously. Further, in some embodiments, some of the operations, actions, acts, blocks, steps, or the like, may be omitted, added, modified, skipped, or the like, without departing from the scope of the disclosure.

Figure 10:
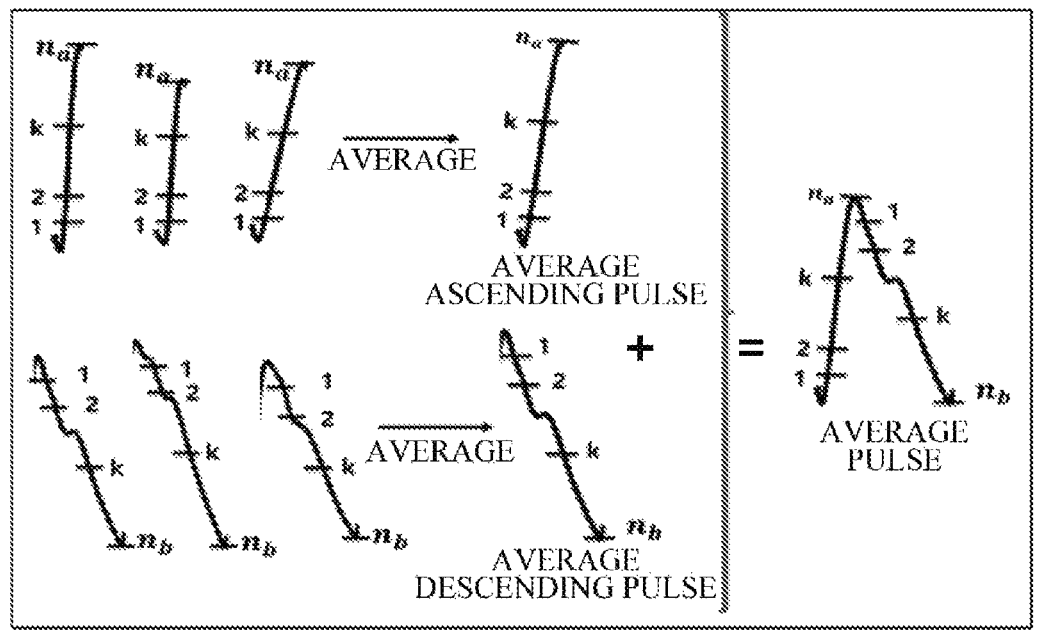
FIG. 10 is an example scenario in which average ascending pulse and average descending pulse are computed and concatenated to obtain a global/local signal pulse denoted as an average pulse, according to an example embodiment.

FIG. 10 is an example scenario in which an average ascending pulse and an average descending pulse are determined and concatenated to obtain a global/local signal pulse denoted as the "average pulse" in FIG. 10, according to an example embodiment.

Initially, the motion artifact correcting engine 140 is configured to determine the average number of samples ($n_a$) in the ascending signals of all of the pulses. $n_a$ is referred to as "average ascending length" in the present disclosure. The motion artifact correcting engine 140 is configured to determine the average number of samples ($n_b$) in the descending signals of all of the pulses. $n_b$ is referred to as "average descending length" in the present disclosure.

Further, the motion artifact correcting engine 140 is configured to resample each ascending pulse to have $n_a$ samples and each descending pulse to have $n_b$ samples. Then the kth pulse is represented as:

$$P_k = \{P_k^{asc}(1), P_k^{asc}(2) \ldots P_k^{asc}(n_a), P_k^{desc}(1), P_k^{desc}(2) \ldots P_k^{desc}(n_b)\}$$

If there are L pulses in the signal, then the entire signal is represented as:

$$S' = P_1 P_2 \ldots P_L$$

Further, the average ascending pulse and average descending pulse are represented respectively as:

$$P_{avg}^{asc}(i) = \text{mean}(P_1^{asc}(i), \ldots, P_L^{asc}(i))$$

$$P_{avg}^{desc}(i) = \text{mean}(P_1^{desc}(i), \ldots, P_L^{desc}(i))$$

As shown above, $P_{avg}^{asc}(i)$ and $P_{avg}^{desc}(i)$ is the $i^{th}$ sample value of the average ascending pulse and ith sample value of the average descending pulse respectively.

Thus the global signal pulse is represented as:

$$P_{avg} = \{P_{avg}^{asc}(1), P_{avg}^{asc}(2) \ldots P_{avg}^{asc}(n_a), P_{avg}^{desc}(1), P_{avg}^{desc}(2) \ldots P_{avg}^{desc}(n_b)\}$$

For each kth pulse $P_k$, the motion artifact correcting engine 140 is configured to compute the M pulse window average, referred to as the local signal pulse represented as:

$$P_k^{wind} = \frac{1}{M+1} \sum_{m=k-M/2}^{k+M/2} P_m,$$

The local signal pulse is effectively the average of M pulses around the kth pulse. For example, the local signal pulse may include (M/2) pulses to the left of the kth pulse and (M/2) pulses to the right of the kth pulse. Further, for the kth pulse, instead of equally weighting all the pulses in the window, a differential weighting scheme that assigns more weight to pulses closer (e.g., more adjacent) to the kth pulse may also be applied.

The intermediate rectified kth pulse is the weighted sum of the global signal pulse and the kth local signal pulse.

$$P_k^{corrected} = aP_{avg} + (1-a)P_k^{wind}$$

$$0 \leq a \leq 1.$$

Based on each pulse being corrected, the motion artifact correcting engine 140 is configured to resample each pulse to its actual (or initial) number of samples as included in the drift removed signal. In this way, vital period information regarding each pulse may be retained.

Figure 11:
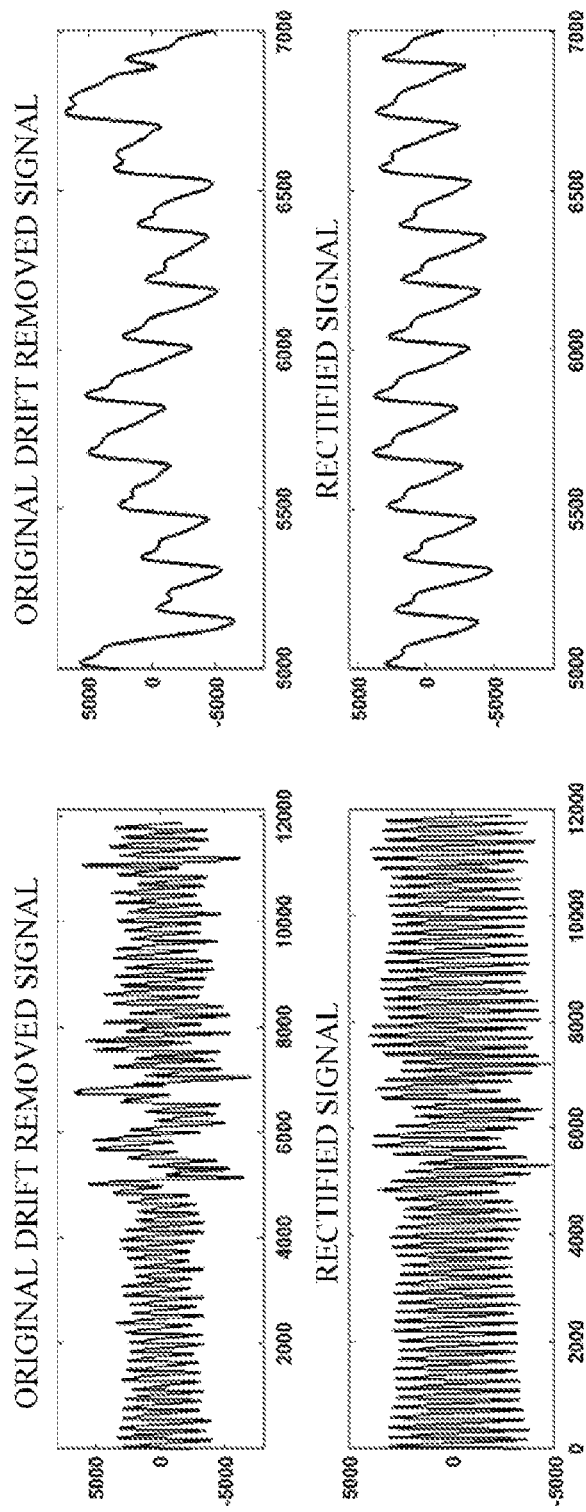
FIG. 11 is graph illustrating an original drift removed signal and the rectified PPG signal for a=0.3, M=3, according to an example embodiment.

FIG. 11 is a diagram illustrating an original drift removed signal and a rectified signal for a=0.3 and M=3. The graphs on the right are snapshots of a section of signal shown in the graphs on the left. As shown in FIG. 11, the perturbations are rectified.

Figure 12:
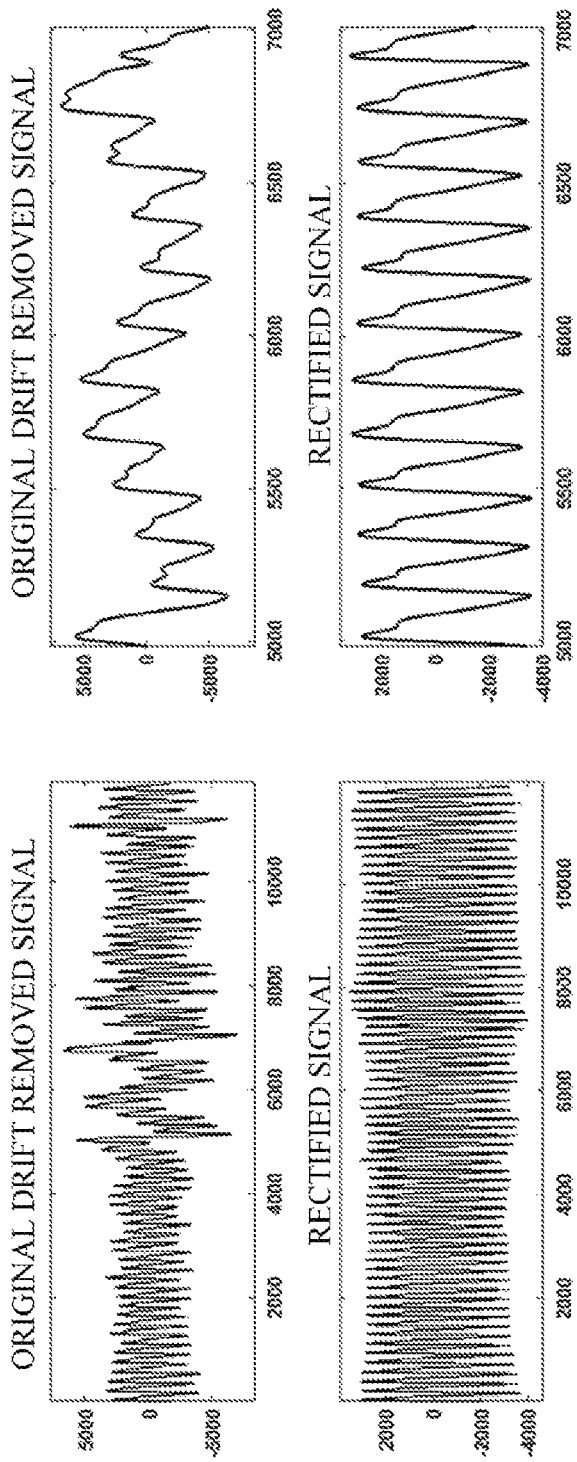
FIG. 12 is graph illustrating the original drift removed signal and the rectified PPG signal for a=0.5, M=5, according to an example embodiment.

FIG. 12 is a diagram illustrating an original drift removed signal and a rectified signal for a=0.5, M=5. The graphs on the right are snapshots of a section of signal shown in the graphs on the left. As shown in FIG. 12, the pulses are more uniform than as compared to the pulses shown in FIG. 11.

Here a and M act as hyper parameters. The greater the value of a and M, the more uniform the pulses may be. The optimal value of a and M may be hyper-tuned using cross validation or may be set based on prior knowledge regarding the signal.

Figure 13:
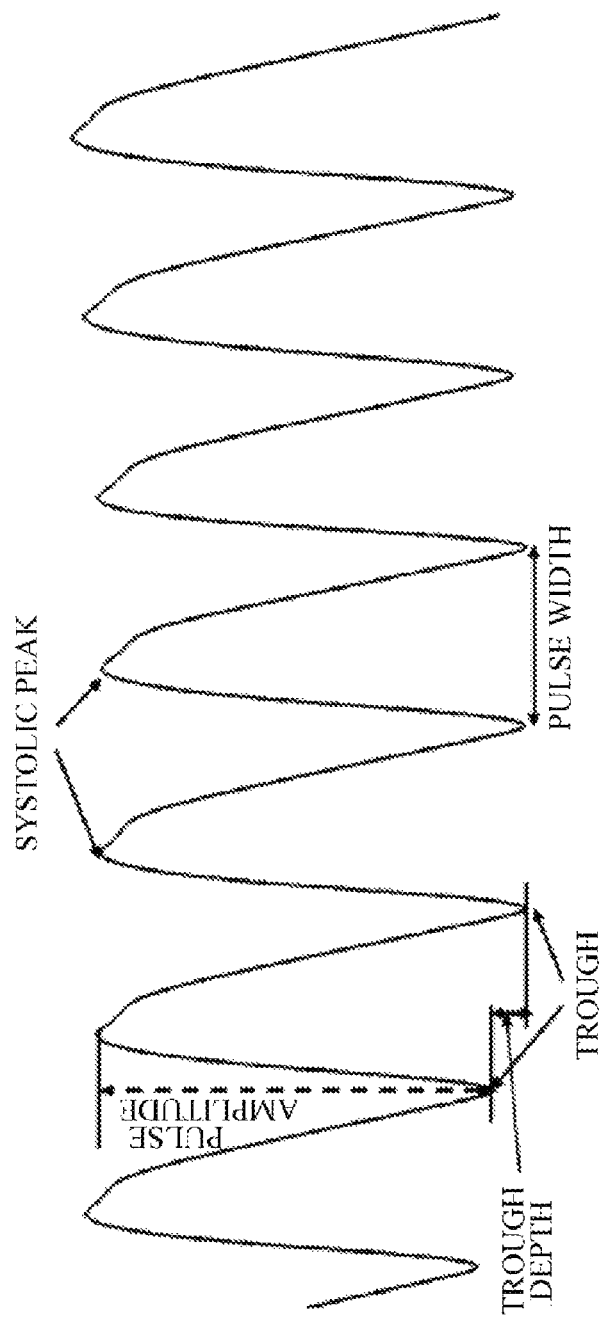
FIG. 13 is graph illustrating characteristics of the PPG signal for defining quality evaluation metrics, according to an example embodiment.

FIG. 13 is a diagram illustrating characteristics of the PPG signal for defining quality evaluation metrics, according to an example embodiment.

In order to determine the performance of the proposed methods, the quality of the processed signal should be assessed. The quality of pre-processed data may be assessed using a pulse amplitude variance and a trough depth variance.

Pulse amplitude may correspond to a height of a pulse peak measured from a preceding trough. Pulse amplitude may be calculated by identifying peaks and troughs in the PPG signal. The differences between the peaks and the troughs may be calculated, and the variance of all the differences may correspond to the pulse amplitude variance.

Trough depth may correspond to an absolute difference between two consecutive troughs. Trough depth may be calculated by identifying troughs between peaks from the PPG signal. The absolute difference of all the identified troughs may be calculated, and the variance of all the differences may correspond to the trough depth variance.

The variations in blood volume might not change drastically over a one minute duration. Therefore, the PPG waveform variations may be similar. This implies that the pulse amplitude variance and trough depth variance should decrease for the pre-processed data.

The example embodiments disclosed herein may be implemented using at least one software program running on at least one hardware device performing network management functions to control the elements.

A number of example embodiments have been described above. However, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method for pre-processing a photoplethysmogram (PPG) signal, the method comprising:
    receiving, by a processor of an apparatus, the PPG signal including a plurality of pulses;
    obtaining, by the processor of the apparatus, a smoothed PPG signal based on smoothing the PPG signal using a moving average filter;
    obtaining, by the processor of the apparatus, a drift removed PPG signal based on removing drift from the smoothed PPG signal using a fitted polynomial function; and
    obtaining, by the processor of the apparatus, a rectified PPG signal based on correcting a motion artifact of the drift removed PPG signal by replacing each of the plurality of pulses using a combination of a global signal pulse and a corresponding local signal pulse.

2. The method of claim 1, further comprising:
    extracting, by the processor of the apparatus, a feature from the rectified PPG signal; and
    predicting, by the processor of the apparatus, a vital signal based on the extracted feature.

3. The method of claim 1, wherein obtaining the drift removed PPG signal comprises:
    determining the fitted polynomial function as a polynomial approximation of a predefined degree of the smoothed PPG signal; and
    subtracting the fitted polynomial function from the smoothed PPG signal to obtain the drift removed PPG signal.

4. The method of claim 1, further comprising:
    dividing each pulse of the drift removed PPG signal into an ascending pulse and a descending pulse based on troughs and peaks of the drift removed PPG signal;
    obtaining an average ascending length as an average of a number of samples in each ascending pulse;
    obtaining an average descending length as an average of a number of samples in each descending pulse;
    resampling each ascending pulse to the average ascending length using linear interpolation to obtain a plurality of resampled ascending pulses;
    resampling each descending pulse to the average descending length using linear interpolation to obtain a plurality of resampled descending pulses;
    obtaining an average ascending pulse as an average of the plurality of resampled ascending pulses;
    obtaining an average descending pulse as an average of the plurality of resampled descending pulses; and
    determining the global signal pulse by concatenating the average ascending pulse and the average descending pulse.

5. The method of claim 1, further comprising:
    isolating a predefined number of local pulses of the drift removed PPG signal around the local pulse to be rectified;
    dividing each of the local signal pulses into a local ascending pulse and a local descending pulse;
    resampling each local ascending pulse to an average ascending length using linear interpolation to obtain a plurality of resampled local ascending pulses;

resampling each local descending pulse to an average descending length using linear interpolation to obtain a plurality of resampled local descending pulses;

obtaining an average local ascending pulse as the average of the plurality of resampled local ascending pulses;

obtaining an average local descending pulse as the average of the plurality of resampled local descending pulses; and determining the local signal pulse by concatenating the average local ascending pulse and the average local descending pulse.

6. The method of claim 1, wherein obtaining the rectified PPG signal comprises:

obtaining an intermediate rectified PPG signal by replacing each local signal pulse using a convex combination of the corresponding local signal pulse and the global signal pulse; and resampling each pulse in the intermediate rectified PPG signal to a number of samples in the corresponding pulse of the drift removed PPG signal.

7. The method of claim 6, wherein resampling each pulse in the intermediate rectified PPG signal to the number of samples in the corresponding pulse of the drift removed PPG signal comprises:

dividing each pulse in the intermediate rectified PPG signal into an ascending pulse and a descending pulse, wherein a number of samples in the ascending pulse is the average ascending length and number of samples in the descending pulse is the average descending length;

resampling each ascending pulse to the number of samples in the ascending pulse of the corresponding pulse in the drift removed PPG signal to obtain a rectified ascending pulse;

resampling each descending pulse to the number of samples in the descending pulse of the corresponding pulse in the drift removed PPG signal to obtain a rectified descending pulse; and concatenating each rectified ascending pulse with the corresponding rectified descending pulse to obtain the rectified PPG signal.

8. The method of claim 4, wherein the troughs and the peaks denote sample indices corresponding to troughs and peaks in the smoothed PPG signal.

9. The method of claim 1, further comprising:

removing peaks that occur before a first trough or after a last trough.

10. The method of claim 2, wherein the feature includes at least one of a mean of a Kaizer Teager Energy (KTE) feature, a variance of the KTE feature, a skewness of the KTE feature, a Spectral Entropy feature, and a Spectral Energy Logarithmic feature.

11. An apparatus for pre-processing a photoplethysmogram (PPG) signal, the apparatus comprising:

a processor configured to:

receive the PPG signal including a plurality of pulses;

obtain a smoothed PPG signal based on smoothing the PPG signal using a moving average filter;

obtain a drift removed PPG signal based on removing drift from the smoothed PPG signal using a fitted polynomial function; and obtain a rectified PPG signal based on correcting a motion artifact of the drift removed PPG signal by replacing each of the plurality of pulses using a combination of a global signal pulse and a corresponding local signal pulse.

12. The apparatus of claim 11, wherein the processor is further configured to:

extract a feature from the rectified PPG signal; and
predict a vital signal based on the extracted feature.

13. The apparatus of claim 11, wherein the processor is further configured to:

determine the fitted polynomial function as a polynomial approximation of a predefined degree of the smoothed PPG signal; and subtract the fitted polynomial function from the smoothed PPG signal to obtain the drift removed PPG signal.

14. The apparatus of claim 11, wherein the processor is further configured to:

divide each pulse of the drift removed PPG signal into an ascending pulse and a descending pulse based on troughs and peaks of the drift removed PPG signal;

obtain an average ascending length as an average of a number of samples in each ascending pulse;

obtain an average descending length as an average of a number of samples in each descending pulse;

resample each ascending pulse to the average ascending length using linear interpolation to obtain a plurality of resampled ascending pulses;

resample each descending pulse to the average descending length using linear interpolation to obtain a plurality of resampled descending pulses;

obtain an average ascending pulse as the average of the plurality of resampled ascending pulses;

obtain an average descending pulse as the average of the plurality of resampled descending pulses; and determine the global signal pulse by concatenating the average ascending pulse and the average descending pulse.

15. The apparatus of claim 11, wherein the processor is further configured to:

isolate a predefined number of local pulses around the pulse to be rectified;

divide each of the local pulses into a local ascending pulse and a local descending pulse;

resample each local ascending pulse to the average ascending length using linear interpolation to obtain a plurality of resampled local ascending pulses;

resample each local descending pulse to the average descending length using linear interpolation to obtain a plurality of resampled local descending pulses;

obtain an average local ascending pulse as the average of the plurality of resampled local ascending pulses;

obtain an average local descending pulse as the average of the plurality of resampled local descending pulses; and determine the local signal pulse by concatenating the average local ascending pulse and the average local descending pulse.

16. The apparatus of claim 11, the processor is further configured to:

obtain an intermediate rectified PPG signal by replacing each local signal pulse using a convex combination of the corresponding local signal pulse and the global signal pulse; and resample each pulse in the intermediate rectified PPG signal to a number of samples in the corresponding pulse of the drift removed PPG signal.

17. The apparatus of claim 16, wherein the processor is further configured to:

divide each pulse in the intermediate rectified PPG signal into an ascending and a descending pulse, wherein a number of samples in the ascending pulse is the average ascending length and a number of samples in the descending pulse is the average descending length;

resample each ascending pulse to the number of samples in the ascending pulse of the corresponding pulse in the drift removed PPG signal to obtain a rectified ascending pulse; and resample each descending pulse to the number of samples in the descending pulse of the corresponding pulse in the drift removed PPG signal to obtain a rectified descending pulse; and concatenate each rectified ascending pulse with the corresponding rectified descending pulse to obtain the rectified PPG signal.

18. The apparatus of claim 14, wherein the troughs and the peaks denote sample indices corresponding to troughs and peaks in the smoothed PPG signal.

19. The apparatus of claim 11, wherein the processor is further configured to:

remove peaks that occur before a first trough or after a last trough.

20. The apparatus of claim 12, wherein the feature includes at least one of a mean of a Kaizer Teager Energy (KTE) feature, a variance of the KTE feature, a skewness of the KTE feature, a Spectral Entropy feature, and a Spectral Energy Logarithmic feature.

\* \* \* \* \*